(12) United States Patent
Rebetez et al.

(10) Patent No.: US 10,527,549 B2
(45) Date of Patent: Jan. 7, 2020

(54) CROSS-TALK CORRECTION IN MULTIPLEXING ANALYSIS OF BIOLOGICAL SAMPLE

(71) Applicant: MYCARTIS N.V., Zwijnaarde (BE)

(72) Inventors: David Rebetez, Cheseaux-sur-Lausanne (CH); David Bernasconi, La Neuveville (CH); Mathieu Gaillard, Lausanne (CH); Didier Falconnet, Vufflens-la-Ville (CH); José Gil, Ecublens (CH)

(73) Assignee: MYCARTIS N.V., Zwijnaarde (BE)

( * ) Notice: Subject to any disclaimer, the term of this patent is extended or adjusted under 35 U.S.C. 154(b) by 0 days.

(21) Appl. No.: 15/754,005

(22) PCT Filed: Sep. 21, 2016

(86) PCT No.: PCT/EP2016/072341
§ 371 (c)(1),
(2) Date: Feb. 21, 2018

(87) PCT Pub. No.: WO2017/050788
PCT Pub. Date: Mar. 30, 2017

(65) Prior Publication Data
US 2018/0275059 A1  Sep. 27, 2018

(30) Foreign Application Priority Data

Sep. 22, 2015 (EP) .................... 15186210

(51) Int. Cl.
*G01N 21/64* (2006.01)
*B01L 3/00* (2006.01)
(Continued)

(52) U.S. Cl.
CPC .... *G01N 21/6452* (2013.01); *B01L 3/502715* (2013.01); *G01N 21/6408* (2013.01);
(Continued)

(58) Field of Classification Search
CPC ............ G01J 3/4406; G01N 2021/058; G01N 2021/6441
See application file for complete search history.

(56) References Cited

U.S. PATENT DOCUMENTS

| | | | | |
|---|---|---|---|---|
| 2008/0241843 | A1* | 10/2008 | Zare | ........................ G01J 3/02 435/6.12 |
| 2011/0306506 | A1* | 12/2011 | Demierre | .......... B01L 3/502761 506/7 |

(Continued)

FOREIGN PATENT DOCUMENTS

WO  WO-2006/015251 A2  2/2006

OTHER PUBLICATIONS

Streit, The effect of interchannel crosstalk on array performance, The Journal of the Acoustical Society of America 86, 1827-1834 (Year: 1989).*

(Continued)

*Primary Examiner* — Michael J Dalbo
(74) *Attorney, Agent, or Firm* — Marshall, Gerstein & Borun LLP

(57) ABSTRACT

A method for determining fluorescence values $\{\varphi_i^{spe}\}_{i \in \{1, 2, \ldots, I\}}$ of a set of I fluorescent microparticles $\{\mu P_i\}_{i \in \{1, 2, \ldots, I\}}$ of a multiplexed analysis, the microparticles being in a monolayer arrangement, includes acquiring a digital fluorescence image of the set of fluorescent microparticles $\{\mu P_i\}_{i \in \{1, 2, \ldots, I\}}$; and computing, for each fluorescent microparticle $\mu P_i$ in the set of fluorescent microparticles $\{\mu P_i\}_{i \in \{1, 2, \ldots, I\}}$, a fluorescence value $\varphi_i^{meas}$ based only on pixels of the acquired image corresponding to said fluorescent microparticle $\mu P_i$. The method includes computing the fluorescence value $\varphi_i^{spe}$ of the fluorescent microparticle $\mu P_i$ by correcting its first fluorescence $\varphi_i^{meas}$ by a cross-talk fluorescence contribution $\varphi_i^{cross}$ in the first (Continued)

fluorescence $\varphi_i^{meas}$ from other fluorescent microparticles $\{\mu P_j\}_{j \neq i}$ in the set of fluorescent microparticles $\{\mu P_i\}_{i \in \{1, 2, \ldots, I\}}$.

13 Claims, 8 Drawing Sheets

(51) Int. Cl.
 *G01J 3/44* (2006.01)
 *G01N 21/05* (2006.01)

(52) U.S. Cl.
 CPC ..... *G01N 21/6428* (2013.01); *G01N 21/6456* (2013.01); *B01L 2300/0627* (2013.01); *G01J 3/4406* (2013.01); *G01N 2021/058* (2013.01); *G01N 2021/6441* (2013.01)

(56) References Cited

U.S. PATENT DOCUMENTS

| | | | |
|---|---|---|---|
| 2012/0015825 A1 | 1/2012 | Zhong et al. | |
| 2012/0315622 A1* | 12/2012 | Rotman | C12Q 1/04 435/5 |
| 2013/0302910 A1* | 11/2013 | Demierre | B01L 3/502761 436/501 |

OTHER PUBLICATIONS

Kannan, Spatially Resolved Total Internal Reflection Fluorescence Correlation Microscopy Using an Electron Multiplying Charge-Coupled Device Camera, Analytical Chemistry, vol. 79, No. 12, Jun. 15, 4463-4470 (Year: 2007).*

Falconnet et al., "Raid, Sensitive and Real-Time Multiplexing Platform for the Analysis of Protein and Nucleic-Acid Biomarkers," *Analytical Chemistry*, pp. 1582-1589 (2015).

International Preliminary Report on Patentability issued in PCT Patent Application No. PCT/EP2016/072341 dated Dec. 20, 2017.

Written Opinion issued in PCT Patent Application No. PCT/EP2016/072341 dated Dec. 1, 2016.

International Search Report issued in PCT Patent Application No. PCT/EP2016/072341 dated Dec. 1, 2016.

Nielsen et al., "High efficiency beam splitter for multifocal multiphoton microscopy," *Journal of Microscopy*, Blackwell Science, vol. 201, (Mar. 2001).

Irawan et al., "Cross-Talk Problem on a Fluorescence Multi-Channel Microfluidic Chip System," *Biomedical Microdevices, Kluwer Academic Publishers*, vol. 7, No. 3 (Sep. 2005).

Pregibon et al., "Multifunctional encoded particles for high-throughput biomolecule analysis," *Science, American Association for the Advancement of Science*, vol. 315, No. 5817 (Mar. 2007).

* cited by examiner

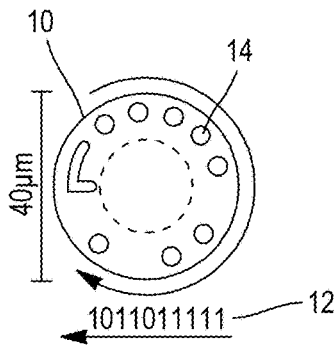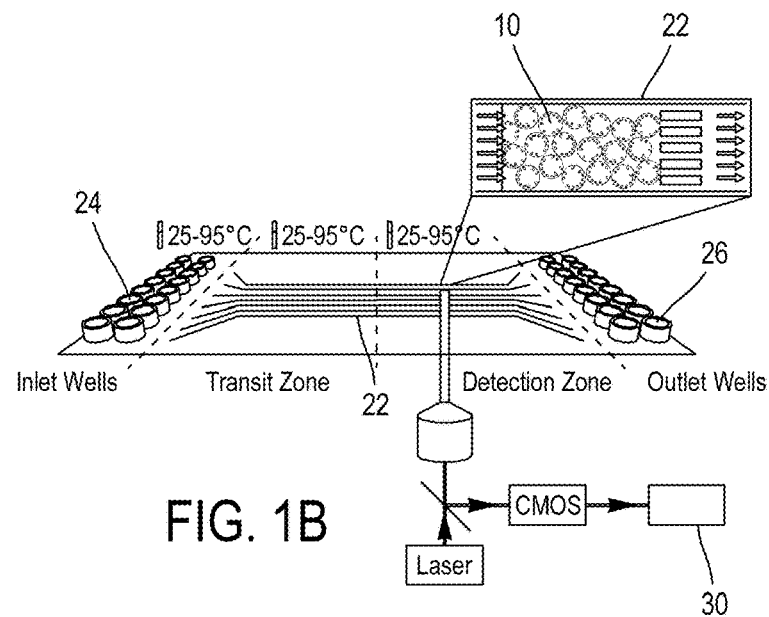
FIG. 1A
FIG. 1B
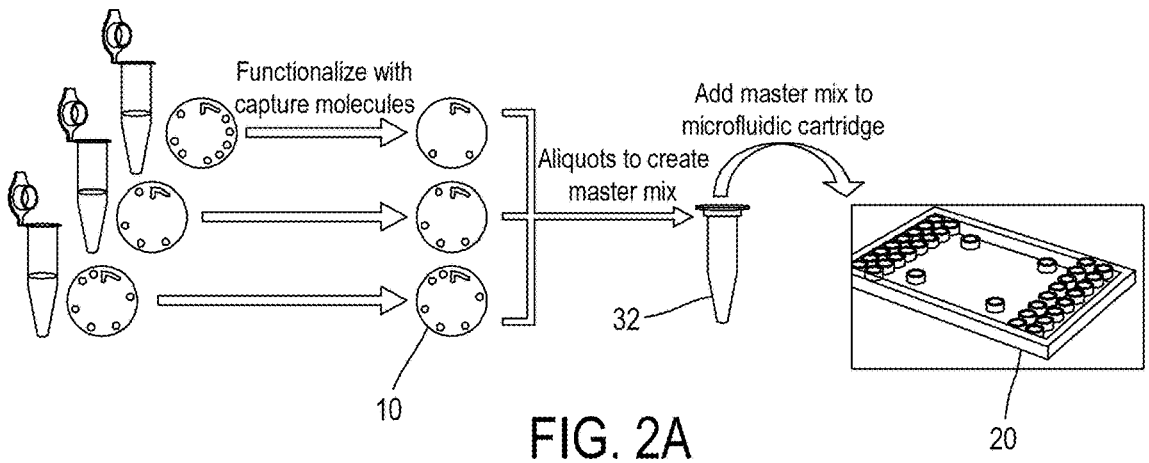
FIG. 2A
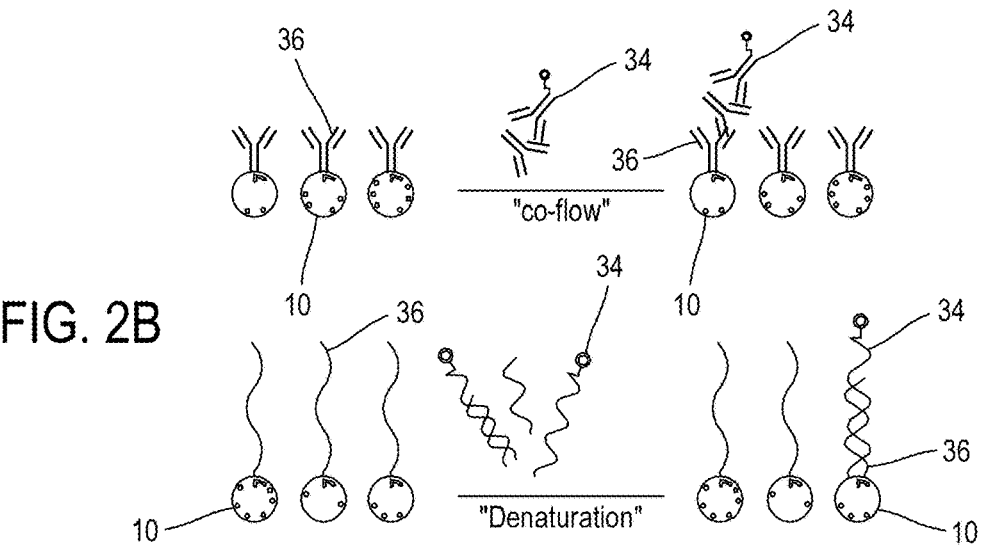
FIG. 2B

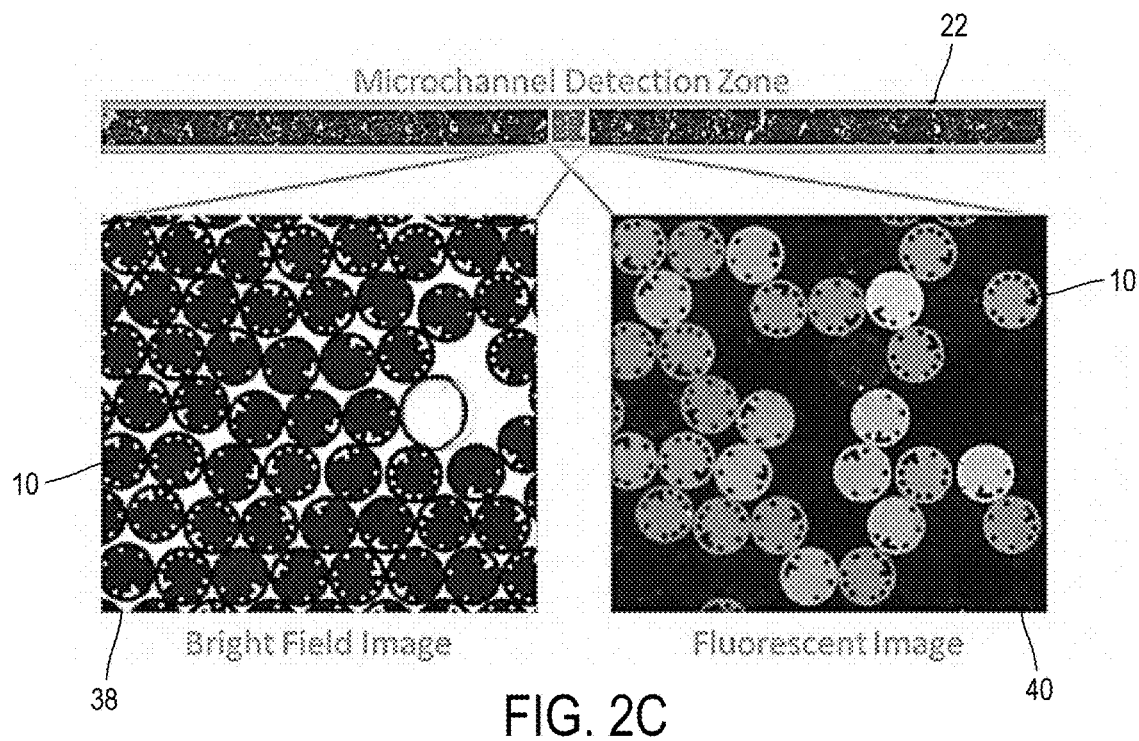
FIG. 2C
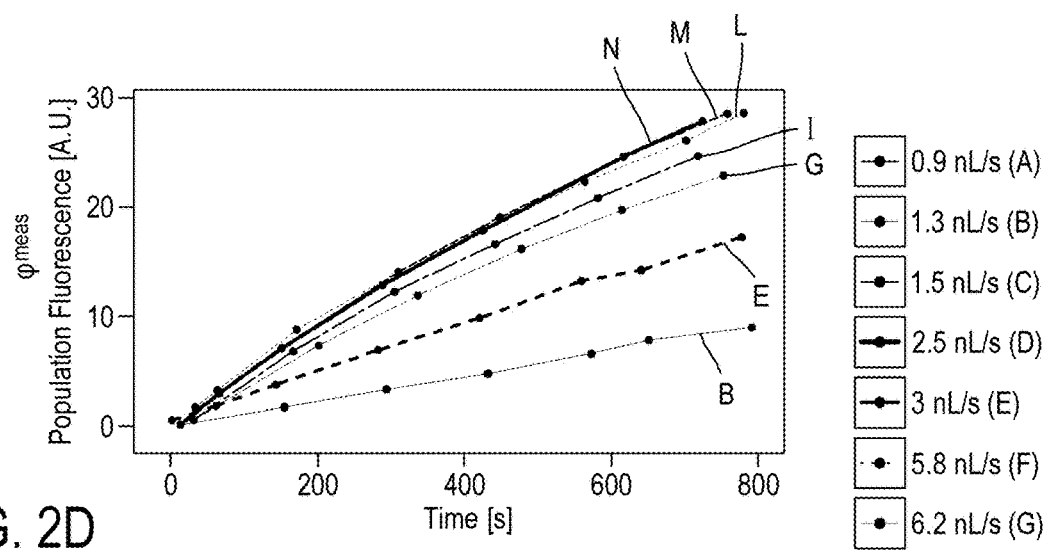
FIG. 2D
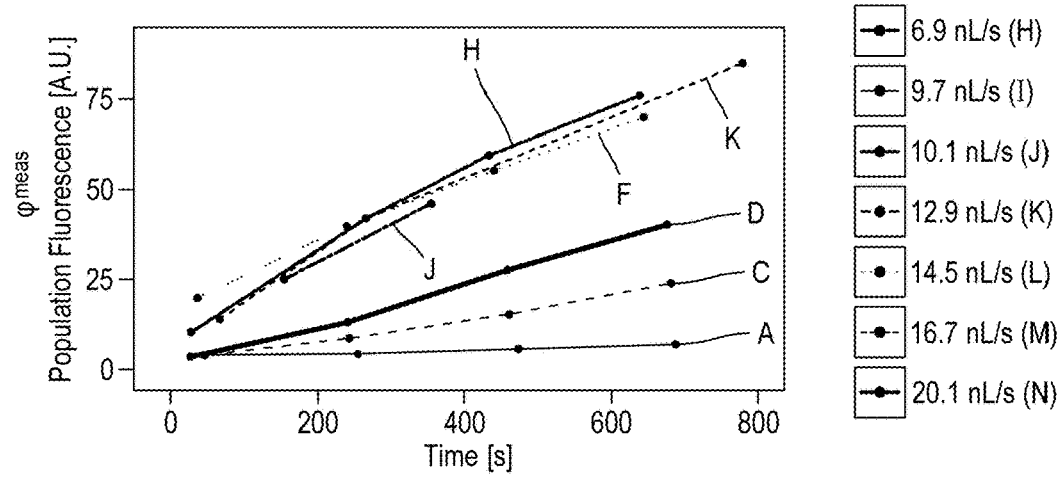

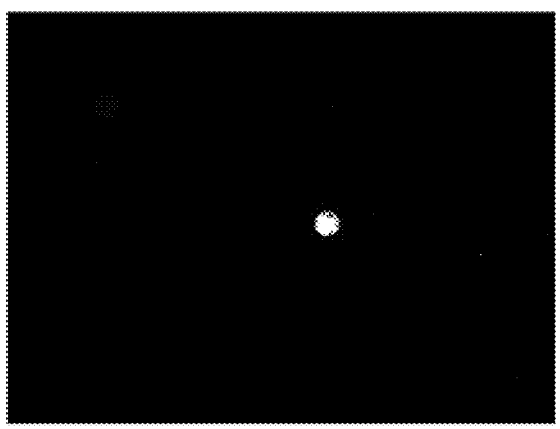 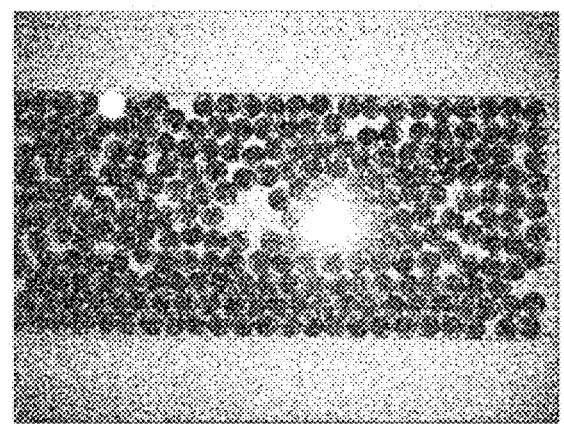
FIG. 4A              FIG. 4B
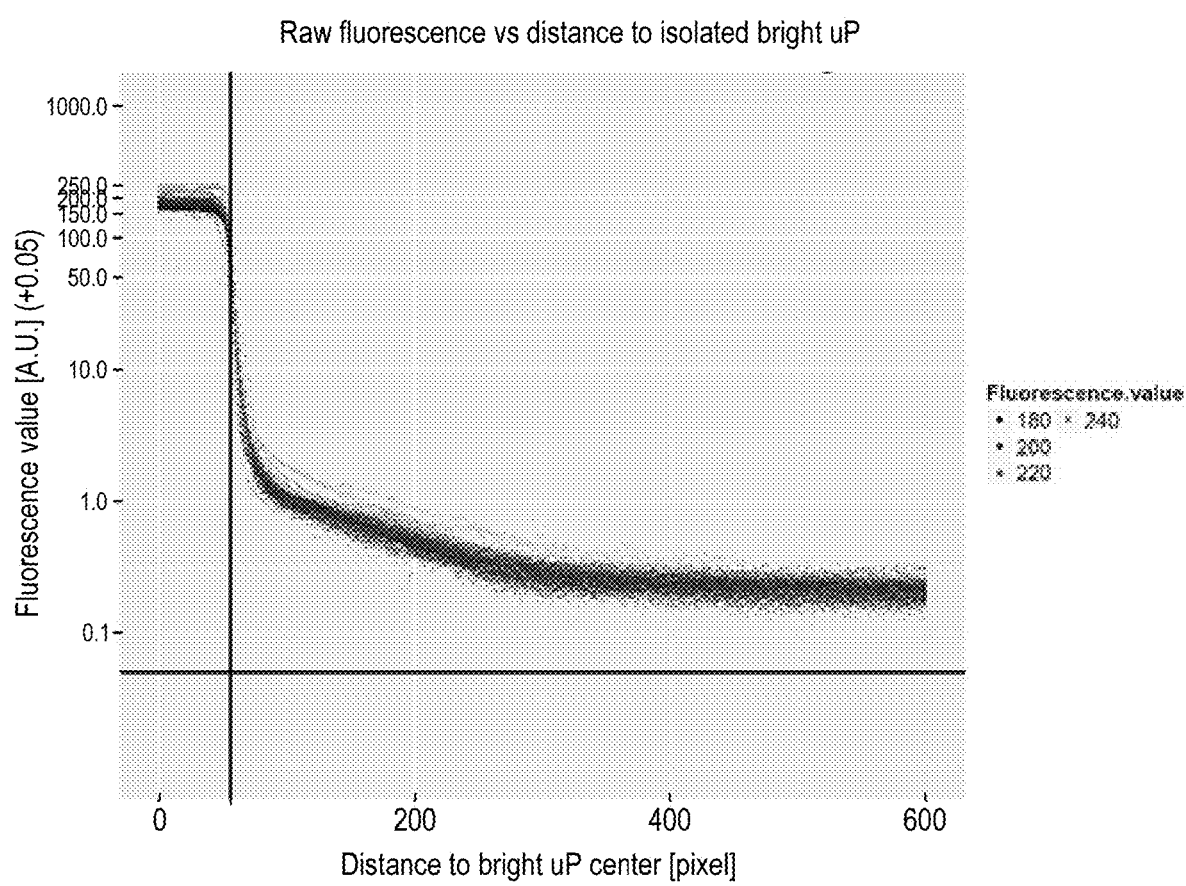
FIG. 5

CROSS-TALK CORRECTION IN MULTIPLEXING ANALYSIS OF BIOLOGICAL SAMPLE

TECHNOLOGICAL FIELD

The present disclosure relates to biological multiplexing analysis, in particular in diagnosis of complex diseases based on detection of multiple biomarkers in a biological sample.

BACKGROUND

Diagnosis of complex diseases and response to treatments are often associated with multiple biomolecules rather than a single identifiable biomarker. In contrast to conventional techniques which measure one analyte at a time, multiplexing technologies may measure, within a single assay, tens to thousands of different biomolecules, e.g., proteins or nucleic acids, from a single biological sample using identical conditions. Basically, capture molecules of different types, e.g. antibodies, target proteins, peptides or nucleic acids, are provided in an assay apparatus filled with the sample, each type of capture molecule being designed to form with the biomarker to be searched in the sample a particular fluorescently labeled complex (usually referred as "the targeted fluorescent labeled biomarker"). One main issue of multiplexing techniques is to determine during the single assay the fluorescence originating from a single type of fluorescently labeled biomarkers bound to their complementary capture molecules (hereafter "individual fluorescence").

Various multiplexing technologies are available, each being usually classified according to its specific encoding strategy addressing this issue. The most popular commercially available multiplexing technologies are array-based and bead-based. In array-based technologies, capture molecules are bound on a panel in a known arrangement to form a 2D array of "capture spots", each dedicated to the capture of a particular biomarker. Such planar arrays thus rely on x-y-coordinates of the capture spots to determine the fluorescence of each biomarker. Bead-based technologies are based on spectral encoding in which the color and intensity allows discriminating each bead population. They have proven to be highly flexible and scalable. However, the currently available bead-based systems are designed to run cost-effectively in batches and the need for waiting on sufficient samples to fill the plate can slow down the turnaround time in routine clinical testing. Furthermore, both technologies suffer from slow binding kinetics, as they are mainly driven by diffusion. This usually imposes long sample incubation times even when agitation is used to speed up the process. In addition, diffusion limited binding regime can also contribute to reported high intra- and interassay variations.

To address the above limitations, a multiplexing technology based on encoded microparticles and microfluidic channels has been designed. This technology is for example described in "*Rapid, Sensitive and Real-Time Multiplexing Platform for the Analysis of Protein and Nucleic-Acid Biomarkers*", Didier Falconnet and al., Anal. Chem. 2015, 87, 1582-1589 and its supporting information downloadable from the website http://pubs.acs.org. One apparatus embodying this technology is sold under the reference named "Evaluation™" by MyCartis, Ghent, BE. The main components of this technology (encoded microparticles, microfluidic channel cartridge and instrumentation) are now briefly described in relation with FIG. 1.

Referring to FIG. 1A, the encoded microparticles 10, or "carriers", are disk-shaped, 40 µm in diameter and 10 µm in height, and are produced from silicon wafers, e.g. using MEMS manufacturing technology. The periphery of each microparticle 10 is unambiguously encoded using a 10-digit binary code $Id_m$ 12, or "identifier", formed by the presence or absence of holes 14. Capture molecules are bound to both faces of the microparticles 10, the latter thus acting as a solid support for a multitude of possible capture molecules, including antibodies, target proteins, peptides, nucleic acids or other biomolecules. More particularly, a single type of capture molecules (i.e. capture molecules dedicated to the capture of a particular biomarker) is tethered onto microparticles sharing the same code $Id_m$.

Referring to FIG. 1B, the cartridge 20, or "assay plate", features a plurality of microscale channels 22 able to host encoded microparticle mixes and thus enabling running multiple samples simultaneously or sequentially (i.e. at different dates). Each channel 22 is made of transparent walls and connects an inlet well 24 and an outlet well 26 which enable the pressurization of the channel 22 above the atmospheric pressure, enabling the microfluidic operation of the channel. The channels 22 are at least 5 times, e.g. 10 times, wider than the microparticles' diameter, and include each a filter structure to restrain the microparticles in a detection zone of the channel. The height of the channels is optimized for efficient microparticle loading and tiling. The shallow channel height prevents microparticles from overlapping each other so that microparticles are arranged in the channel in a monolayer arrangement with one of their faces fully acquirable for imaging purpose. This monolayer arrangement of microparticles in the channel thus enables the use of high resolution imaging for both decoding and fluorescence quantification. Each channel can be loaded with up to thousands of microparticles, a fully loaded channel enabling a multiplexing of more than one hundred different biomarkers with tens of microparticles for each biomarker to be searched for. For multiplexing analysis purpose, a microparticle mix loaded in a channel includes multiple microparticles sharing an identical code, thereby forming a population which provides measurement redundancy for statistical confidence.

Instrumentation aims at acquiring images of the channel, at controlling the fluid actuation and the temperature in the channels and at analyzing acquired images. More particularly, instrumentation comprises:

an optical system 28, with for example a long-working distance objective and a high-sensitivity CMOS camera, to acquire bright field and epi-fluorescence images (e.g. excitation at 640 nm, e.g. using a laser) of the detection zone of the cartridge. The objective is mounted on an automated x-y-z stage for scanning each channel either during the assay for real-time readout or in end point;

lighting system (not illustrated) for uniformly illuminate the detection zone in order to get a high contrast image of the microparticles in bright background for decoding purpose;

a controlling unit (not illustrated) for controlling the microfluidic operation of the cartridge (inlet/outlet wells, pressurization, temperature . . . ), as well as the operation of the optical system;

a computing unit 30 (e.g. personal computer, a server, or more generally any computing hardware configured to receive data from the camera and process the data according to instructions stored on a memory . . . ), possibly part of the controlling unit or independent therefrom, coupled to the camera for receiving images thereof and running an multiplexing analysis computing program to automatically quantify the biomarkers in the tested sample based on the fluorescent and bright-light images acquired by the optical system.

Referring to FIGS. 2A-2E, a multiplex analysis embodied by the aforementioned multiplexing technology thus consists in:

producing a suspension mix of microparticles 32, the microparticles 10 being chosen based on the biomarkers to be searched for in a tested sample and loading the liquid mix of microparticles 32 in the cartridge 20 to fill one or more channels 22 so that a planar arrangement of the microparticle is provided for optimal readout purpose (FIG. 2A);

loading the tested liquid sample, along with, if required, reagents (e.g. for sandwich reactions), in the channels 22, thereby initiating incubation and/or binding reaction in microfluidic environment between the biomarkers 34 in the tested sample and the capture molecules 36 bound to the microparticles 10 (FIG. 2B);

acquiring images of the detection zone of the channels 22 (e.g. in real time or once at the end of the process). While the microparticles 10 are immobilized in the channels 22 thanks to pressurization and filter elements, a cycle of image acquisition preferably consists in acquiring consecutively a bright field image 38 and a fluorescence image 40 or vice versa, so that the position of each microparticles is the same in both images (FIG. 2C);

for each channel 22 and for each pair of bright field and a fluorescence images 38, 40 of the channel:

analyzing the bright field image 38 to identify location $X_i$ of each microparticle 10 in the channels 22 and to read the code $Id_m$ 12 of each microparticle 10;

analyzing the fluorescence image 40 to determine the fluorescence $\varphi^{meas}$ of each microparticle 10 in the fluorescent image (e.g. corresponding to the maximum of a kernel density fitted on the pixels of the portion of the image corresponding to the central portion of the microparticle);

for each channel 22 and each population of microparticles 10 sharing the same code $Id_m$ in the channel:

computing an aggregate value of fluorescence $\varphi^{pop}$ for the population, e.g.: applying a Tukey's boxplot filter on fluorescences $\varphi^{meas}$ to filter out abnormal fluorescence values $\varphi^{meas}$ and thereafter computing the aggregate value as the arithmetic mean value of the remaining fluorescences $\varphi^{meas}$ (FIG. 2D);

determining the biomarker concentration [b] in the tested sample (or "titration") based on the aggregate value $\varphi^{pop}$ using a stored relationship fluorescence versus concentration (e.g. table, analytic mathematical model, ...) determined beforehand for the biomarker and stored in a digital memory of the computing unit 30 (FIG. 2E).

The computed concentrations are then displayed to the user and/or stored on a digital memory (e.g.: the one of the computing unit).

This multiplexing technology allows (i) short assay times and high reproducibility thanks to reaction-limited binding regime, (ii) dynamic control of assay conditions and real-time binding monitoring allowing optimization of multiple parameters within a single assay run, (iii) compatibility with various immunoassay formats such as co-flowing the samples and detection antibodies simultaneously and hence simplifying workflows, (iv) analyte quantification based on initial binding rates leading to increased system dynamic range and (v) high sensitivity via enhanced fluorescence collection, (vi) opportunity to run monoplex (i.e. providing only one type of capture molecules for the quantitative measure of a particular biomarker) assay if desired.

However, in some instances, one observes divergence between a biomarker concentration [b] which is computed from multiplex assay data and the biomarker concentration [b] computed from monoplex assay data.

SUMMARY OF THE DISCLOSURE

One aim of the disclosed embodiments is to propose, in a multiplexing analysis, computation of microparticle fluorescences that corrects the difference between multiplex and monoplex assays.

To this end, one object of the disclosed embodiments is a method for determining fluorescences $\{\varphi_i^{spe}\}_{i \in \{1, 2, \ldots, I\}}$ of a set of I fluorescent microparticles $\{\mu P_i\}_{i \in \{1, 2, \ldots, I\}}$ of a multiplexing analysis, said microparticles being in a monolayer arrangement, the method comprising:

acquiring a digital fluorescence image of the set of fluorescent microparticles $\{\mu P_i\}_{i \in \{1, 2, \ldots, I\}}$; and computing, for each fluorescent microparticle $\mu P_i$ in the set of fluorescent microparticles $\{\mu P_i\}_{i \in \{1, 2, \ldots, I\}}$, a first fluorescence $\varphi_i^{meas}$ based only on pixels of the acquired image corresponding to said fluorescent microparticle $\mu P_i$, According to the disclosed embodiments, the method comprises computing the fluorescence $\varphi_i^{spe}$ of said fluorescent microparticle $\mu P_i$ by correcting its first fluorescence $\varphi_i^{meas}$ by a cross-talk fluorescence contribution $\varphi_i^{cross}$ in said first fluorescence $\varphi_i^{meas}$ from other fluorescent microparticles $\{\mu P_j\}_{j \neq i}$ in the set of fluorescent microparticles $\{\mu P_i\}_{i \in \{1, 2, \ldots, I\}}$.

In other words, the portion of the acquired image corresponding to a microparticle $\mu P_j$ does not strictly correspond to the light produced by said microparticle. Each microparticle produces light that scatters and thus superimposes to the light of other microparticles. Drawing a parallel with imagery, there is a "cross-talk" effect between the microparticles. In particular, the cross-talk effect may be observed when at least two populations of microparticles of different fluorescences (e.g. a dark population and a bright population) are mixed together. For example, when the difference in fluorescence is large enough between the two populations, an increase in fluorescence is observed on some microparticles of the darker populations that are in the neighborhood of microparticles of the brighter population. Cross-talk may also exist in monoplex assay.

According to one embodiment, the computation of the fluorescence value $\varphi_i^{spe}$ comprises:

computing a position $X_i$ in the digital fluorescence image for each fluorescent microparticle $\mu P_i$ in the set of fluorescent microparticles $\{\mu P_j\}_{i \in \{1, 2, \ldots, I\}}$;

modelling the first fluorescence value $\varphi_i^{meas}$ as a function of the positions $\{X_i\}_{i \in \{1, \ldots, I\}}$ and fluorescence values $\{\varphi_i^{spe}\}_{i \in \{1, \ldots, I\}}$ of all fluorescent microparticles $\{\mu P_i\}_{i \in \{1, 2, \ldots, I\}}$; and computing the inverse of said function to obtain the fluorescence value $\varphi_i^{spe}$.

According to one embodiment, the computation of fluorescence $\varphi_i^{spe}$ is carried on based on the following relationship:

$$\varphi_i^{meas} = \varphi_i^{spe} + \sum_{j \neq i} (\alpha_{ij} \cdot \varphi_j^{spe})$$

wherein $\varphi_j^{spe}$ is the fluorescence of the $j^{th}$ fluorescent microparticle $\mu P_j$, and $\alpha_{ij}$ is a unitary cross-talk fluorescence contribution in the first fluorescence $\varphi_i^{meas}$ of the $j^{th}$ fluorescent microparticle µP$_j$, the unitary cross-talk fluorescence contribution α$_{ij}$ depending only on the distance between the fluorescent microparticles µP$_i$ and µP$_j$.

In other words, for a given microparticle, light produced by other microparticles does not reduce to a uniform background noise that one could measure (e.g. by computing the average of the image's brightness) and subtract from the fluorescence of the microparticle. The inventors have further noticed that disturbance from other microparticles is variable, depending on the particular arrangement of the microparticles. To correct the cross-talk effect on a microparticle, embodiments thus compute the contribution of each other microparticles. Accounting for each said contributions results in multiplex measure that is similar to monoplex measure, even for high contrast conditions amongst microparticles.

Moreover, the inventor noticed that the cross-talk effect may be modelled by the sum of isotropic decay profiles. This implies that one may consider a microparticle independently from the other for computing its contribution and that the fluorescence scattered by a microparticle depends only on the distance from the microparticle and the fluorescence on the microparticle. The unitary cross-talk fluorescence contributions α$_{ij}$ corresponds for example to the normalized fluorescence that a microparticle generates and is computed based on constant parameters determined beforehand, for example by the manufacturer of a multiplex analyzer, and stored in the memory of the analyzer.

In particular, the method comprises:
computing a distance d$_{i,j}$ between the i$^{th}$ and the j$^{th}$ fluorescent microparticles in the digital fluorescence image;
for each couple of microparticles (µP$_i$,µP$_j$) in the set of I fluorescent microparticles, computing the unitary cross-talk fluorescence contribution α$_{ij}$ of said couple (µP$_i$,µP$_j$) based on the distance d$_{i,j}$;
computing the fluorescences $\{\varphi_i^{spe}\}_{i\in\{1, 2, \ldots, I\}}$ of the set of fluorescent microparticles $\{\mu P_i\}_{i\in\{1, 2, \ldots, I\}}$ based on the following relationship:

$$\begin{pmatrix} \varphi_1^{spe} \\ \varphi_2^{spe} \\ \vdots \\ \varphi_{I-1}^{spe} \\ \varphi_I^{spe} \end{pmatrix} = \begin{pmatrix} 1 & \alpha_{12} & \cdots & \alpha_{1(I-1)} & \alpha_{1I} \\ \alpha_{21} & 1 & \cdots & \alpha_{2(I-1)} & \alpha_{2I} \\ \vdots & \vdots & \ddots & \vdots & \vdots \\ \alpha_{(I-1)1} & \alpha_{(I-1)2} & \cdots & 1 & \alpha_{(I-1)I} \\ \alpha_{I1} & \alpha_{I2} & \cdots & \alpha_{I(I-1)} & 1 \end{pmatrix}^{-1} \begin{pmatrix} \varphi_1^{meas} \\ \varphi_2^{meas} \\ \vdots \\ \varphi_{I-1}^{meas} \\ \varphi_I^{meas} \end{pmatrix}$$

In other words, the computation is based on a two particular reductions, as it will be discussed later, which enables a simple, while very accurate, correction of the cross-talk effect.

In particular, the unitary cross-talk fluorescence of the j$^{th}$ microparticle in the first fluorescence $\varphi^{meas}$ of the i$^{th}$ fluorescent microparticle is computed based on the following relationship:

$$\alpha_{i,j} = \sum_{n=1}^{N} \left( \theta_n \cdot e^{-k_n(d_{i,j}-\beta_n)} \right)$$

wherein N is an integer greater or equal to 2, θ$_n$, k$_n$ and β$_n$ are predetermined parameters.

Sum of exponential functions is an effective way to model the unitary cross-talk fluorescence contribution α$_{ij}$, while at the same time offering flexibility of convex optimization for computing parameters θ$_n$, k$_n$ and β$_n$. In particular, three exponentials are sufficient to compute α$_{ij}$.

In one embodiment, each fluorescent microparticle µP$_i$ of the set of fluorescent microparticles $\{\mu P_i\}_{i\in\{1, 2, \ldots, I\}}$ comprises an identifier Id$_m$(i) of a set of M different unique identifiers $\{id_m\}_{m\in\{1, 2, \ldots, M\}}$, said identifiant Id$_M$(i) being readable through processing of a digital image of said fluorescent microparticle µP$_i$, and in that the method further comprises:
acquiring a digital image of the set of fluorescent microparticles $\{\mu P_i\}_{i\in\{1, 2, \ldots, I\}}$;
reading the identifier Id$_m$(i) of each microparticle µP$_i$ in the digital image; and
for each identifier Id$_m$ of the set of M different unique identifiers $\{id_m\}_{m\in\{1, 2, \ldots, M\}}$, computing an aggregate fluorescence $\varphi_m^{ag}$ based on the fluorescences $\varphi_i^{spe}$ of the fluorescent microparticles comprising said identifier.

In particular, each fluorescent microparticle µP$_i$ of the set of fluorescent microparticles $\{\mu P_i\}_{i\in\{1, 2, \ldots, I\}}$ comprises a surface coated with fluorescent complexes uniquely associated to the identifiant Id$_m$(i) of said fluorescent microparticle µP$_i$, said complexes comprising first non-fluorescent molecules fixed to the microparticles and second fluorescent molecules bound to the first non-fluorescent molecules.

More particularly, the microparticles have equal dimension.

In a variation, the method comprises:
prior to acquiring the digital fluorescence image of the set of fluorescent microparticles $\{\mu P_i\}_{i\in\{1, 2, \ldots, I\}}$:
disposing in a channel the microparticles without any second fluorescent molecules bound to the first non-fluorescent molecules, so as to arrange the microparticles in a monolayer; and
filling the channel with a liquid sample,
computing concentration of second fluorescent molecules in the sample based on the aggregate fluorescences $\varphi_m^{ag}$.

Another object of the disclosed embodiments is a system for embodying the aforementioned method, in particular a system for determining fluorescences $\{\varphi_i^{spe}\}_{i\in\{1, 2, \ldots, I\}}$ of a set of I fluorescent microparticles $\{\mu P_i\}_{i\in\{1, 2, \ldots, I\}}$ comprising:
at least one channel for receiving the set of I fluorescent microparticles $\{\mu P_i\}_{i\in\{1, 2, \ldots, I\}}$ in a monolayer arrangement;
an acquisition unit for acquiring a digital fluorescent image of the monolayer arrangement of the set fluorescent microparticles $\{\mu P_i\}_{i\in\{1, 2, \ldots, I\}}$ in the channel;
a computing unit for computing the fluorescences $\{\varphi_i^{spe}\}_{i\in\{1, 2, \ldots, I\}}$ based on the acquired digital fluorescent image, the computing unit computing a first fluorescence $\varphi^{meas}$ based only on pixels of acquired digital fluorescent image corresponding to said fluorescent microparticle µP$_i$,
characterized in that the computing unit computes, for each fluorescent microparticle µP$_i$ in the set of fluorescent microparticles $\{\mu P_i\}_{i\in\{1, 2, \ldots, I\}}$:
a cross-talk fluorescence contribution $\varphi_i^{cross}$ in the first fluorescence $\varphi_i^{meas}$ of said fluorescent microparticle µP$_i$ from other fluorescent microparticles $\{\mu P_j\}_{j\neq i}$ in the set of fluorescent microparticles $\{\mu P_i\}_{i\in\{1, 2, \ldots, I\}}$, said computing being based on first fluorescences $\{\varphi_i^{meas}\}_{i\neq t}$ of said other microparticles; and
the fluorescence $\varphi_i^{spe}$ of said fluorescent microparticle µP$_i$ by correcting its first fluorescence $\varphi_i^{meas}$ by the cross-talk fluorescence contribution $\varphi_i^{cross}$.

BRIEF DESCRIPTION OF THE FIGURES

The presently described embodiments will be better understood on reading of the following description provided as an example only in relation with the accompanying drawings, where the same reference numerals designate the same or similar elements, among which:

FIGS. 1A and 1B are schematic views of an encoded microparticle and a multiplex analyzer, respectively, using such a microparticle of the state of the art;

FIGS. 2A-2E illustrate a multiplex analysis of a sample using the microparticle and analyzer of FIGS. 1A and 1B;

FIGS. 4A and 4B illustrate an arrangement of microparticles for determining a fluorescence decay profile;

FIGS. 5 and 6 illustrate respectively the fluorescence decay profile and the relative fluorescence decay profile;

DETAILED DESCRIPTION

Figure 2E:
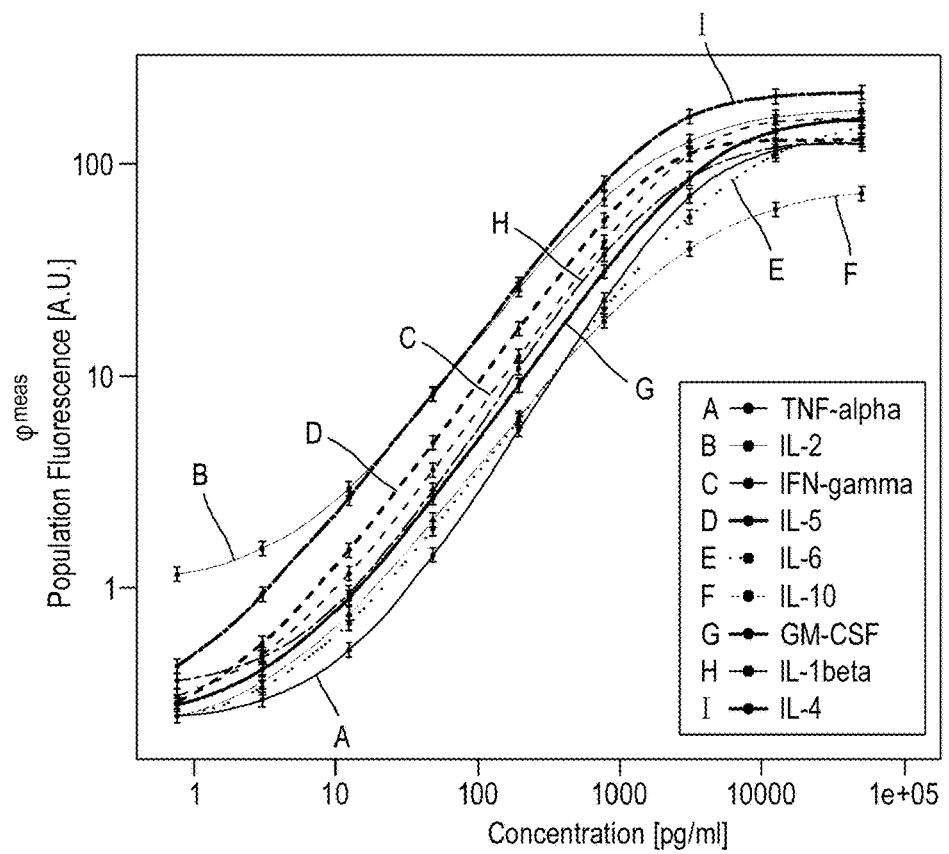
Figure 3:
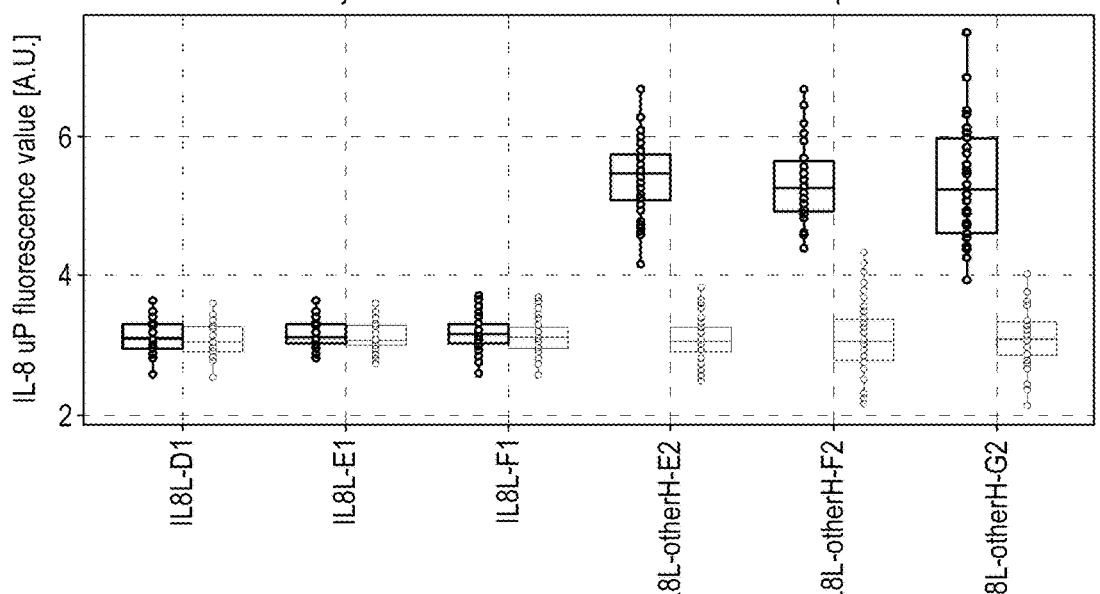
FIG. 3 illustrates differences in fluorescences from a monoplex and multiplex assays.

An embodiment, based on the Evalution™ system detailed above, is now described. The embodiment differs from the Evalution™ system by supplementary processing. In particular, computer instructions and parameters are stored in the memory of the "Evalution™" system to process the acquired digital fluorescence images of the channels so as to correct the cross-talk effect in the fluorescence $\varphi_i^{meas}$ computed by the system. The corrected fluorescences $\varphi^{spec}$ are then used to compute the aggregate values of fluorescence $\varphi^{pop}$ for the populations and the biomarker's concentrations [b] in the tested sample.

In particular, in a set of microparticles $\{\mu P_i\}_{i \in \{1, 2, \ldots, I\}}$ in a channel 22 of the cartridge 20, the measured fluorescence $\varphi_i^{meas}$ of a particular microparticle $\mu P_i$ equals:

$$\varphi_i^{meas} = \varphi_i^{spe} + \varphi_i^{cross} \quad (1)$$

where the fluorescence $\varphi_i^{spe}$ of a microparticle $\mu P_i$ corresponds to the fluorescence produced by the microparticle $\mu P_i$ only and $\varphi_i^{cross}$ is the fluorescence from other microparticles $\{\mu P_j\}_{j \neq i}$ that superimpose to the fluorescence $\varphi_i^{spe}$, that is to say the cross-talk contribution from said other microparticles $\{\mu P_i\}_{j \neq i}$.

According to the described embodiments, the cross-talk contribution $\varphi_i^{cross}$ is modeled as a sum of individual contributions, each having an isotropic decay profile, that is to say:

$$\varphi_i^{cross} = \sum_{j \neq i} (\alpha_{ij} \cdot \varphi_j^{spe}) \quad (2)$$

where $\alpha_{ij}$ is a unitary cross-talk fluorescence contribution in the first fluorescence $\varphi_i^{meas}$ of the $j^{th}$ fluorescent microparticle $\mu P_j$ depending only on the distance $d_{i,j}$ between microparticles $\mu P_i$ and $\mu P_j$, for example the distance between the respective centers of the microparticles.

The fluorescences $\varphi_j^{spe}$ not being available, for the cross-talking effect correction, they are approximated by $\varphi_j^{spe} = \varphi_i^{meas}$, which gives the relation:

$$\varphi_i^{meas} = \varphi_i^{spe} + \sum_{j \neq i} (\alpha_{ij} \cdot \varphi_j^{meas}) \quad (3)$$

In a first variant, $\varphi_i^{spe}$ is thus computed according to:

$$\varphi_i^{spe} = \varphi_i^{meas} - \sum_{j \neq i} (\alpha_{ij} \cdot \varphi_j^{meas}) \quad (4)$$

While this variant shows good results in correcting the cross-talk effect, a better correction is done by the following computation.

In particular, by posing $\forall i$, $\alpha_{ii} = 1$ and storing the $\alpha_{ij}$ in a matrix A, one gets:

$$A = \begin{pmatrix} 1 & \alpha_{12} & \cdots & \alpha_{1(I-1)} & \alpha_{1I} \\ \alpha_{21} & 1 & \cdots & \alpha_{2(I-1)} & \alpha_{2I} \\ \vdots & \cdots & \ddots & \cdots & \vdots \\ \alpha_{(I-1)1} & \alpha_{(I-1)2} & \cdots & 1 & \alpha_{(I-1)I} \\ \alpha_{I1} & \alpha_{I2} & \cdots & \alpha_{I(I-1)} & 1 \end{pmatrix} \quad (5)$$

$$\begin{pmatrix} \varphi_1^{meas} \\ \varphi_2^{meas} \\ \vdots \\ \varphi_{I-1}^{meas} \\ \varphi_I^{meas} \end{pmatrix} = A \begin{pmatrix} \varphi_1^{spe} \\ \varphi_2^{spe} \\ \vdots \\ \varphi_{I-1}^{spe} \\ \varphi_I^{spe} \end{pmatrix} \quad (5)$$

All the fluorescences $\varphi_i^{spe}$ are thus computed together according to:

$$\begin{pmatrix} \varphi_1^{spe} \\ \varphi_2^{spe} \\ \vdots \\ \varphi_{I-1}^{spe} \\ \varphi_I^{spe} \end{pmatrix} = A^{-1} \begin{pmatrix} \varphi_1^{meas} \\ \varphi_2^{meas} \\ \vdots \\ \varphi_{I-1}^{meas} \\ \varphi_I^{meas} \end{pmatrix} \quad (6)$$

As it will be discussed more in detail later, the unitary cross-talk fluorescence contributions $\alpha_{ij}$ are computed according the following relation:

$$\alpha_{ij} = \sum_{n=1}^{N} \left( \theta_n \cdot e^{-k_n (d_{i,j} - \beta_n)} \right) \quad (7)$$

where N is an integer greater or equal to 2, $\theta_n$, $k_n$ and $\beta_n$ are predetermined parameters identical whatever the microparticles, which are stored in the memory of the computing unit 30.

In particular regarding the microparticles of the Evalution™ system, N=3 shows good results in approximating the $\alpha_{ij}$.

Based on the above, according to one embodiment, the computing unit 30 thus computes:

the positions of the center of each microparticles (e.g. the center of the disk-shaped microparticles) in the acquired digital fluorescent image of the channel and thereafter computes for each couples of microparticles $(\mu P_i, \mu P_j)$ in said image the distance $(\mu P_i, \mu P_j)$;

the unitary cross-talk fluorescence contributions $\alpha_{ij}$ according to relation (7);

the matrix A according to relation (5) and its inverse $A^{-1}$;

the fluorescences $\varphi_i^{spe}$ according to relation (6).

Determination of the unitary cross-talk fluorescence contribution is now described in relation to FIGS. 4 to 7. A first step consists in creating at least one large field of view containing only one bright microparticle. To take into account possible influence of the multiplexing environment and microparticles' attributes, a bi-plex assay with a low number of bright microparticle (e.g. fully bright biotin-RPE microparticle) a high number of dark microparticles (e.g. COOH microparticles) is performed and a bright field image and a digital fluorescent image of the microparticles are acquired. By doing so, the decay profile of crosstalk can be measured on the pixels of the image ("the pixels") corresponding to the COOH microparticles around a bright isolated microparticle. A bright microparticle is considered isolated if the closest bright microparticle is at least at 1000 pixels away. Moreover, for increasing accuracy of the computation, only bright microparticles that have a minimum fluorescence $\varphi^{meas}$ and that have homogeneous distribution of fluorescence on their surfaces (e.g. according a coefficient of variation of the pixels of the bright mircroparticle) are kept. A fluorescence image of an isolated bright microparticle surrounded by dark microparticles is illustrated in FIG. 4A. FIG. 4B illustrates the same image with a post-processing over-exposition to show the COOH microparticles.

In a second step, in order to measure the influence on pixels at a distance from the center of the bright microparticle, all the pixels corresponding to the dark microparticles at a distance between d and d+p (where p is a predefined step, e.g. equal to 1), are pooled together in a bin and their mean fluorescence and mean distance to the center of the bright microparticles are computed. The pixels of the dark microparticles are selected with the bright field image.

In FIG. 5, the computed mean fluorescence is plotted over the computed mean distance. Each point on the plot corresponds to the average fluorescence of pixels at a given distance from one isolated bright microparticle. The plateau on the right of the x-axis corresponds to the bright microparticle whose radius is shown by the black vertical line. The fluorescence after said line thus corresponds to a halo of fluorescence surrounding the bright microparticle, which halo has a fluorescence decay profile.

Figure 6:
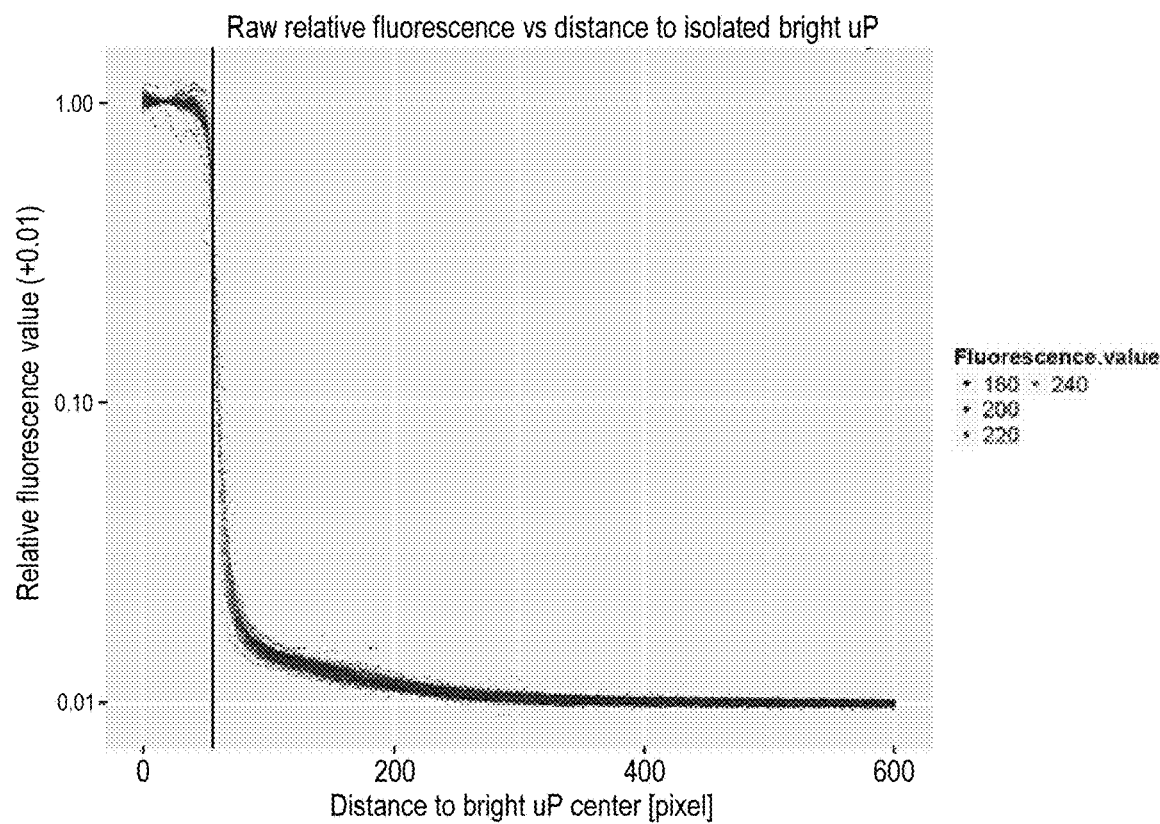

In order to make the profiles comparable among the different conditions, the relative fluorescence is computed by dividing the bin's means fluorescence by the fluorescence of the bright microparticle. FIG. 6 illustrates the relative fluorescence decay profiles corresponding to the one of FIG. 5. The values on the Y-axis of FIG. 6 can be interpreted as the proportion of the fluorescence of the bright microparticle that cross-talks at a given distance from the center of the bright microparticle.

Determination of the relative fluorescence decay profiles has been done for different exposure times, different buffers, instruments and microparticles in order to assess the potential sources of variability. This study shows that the decay profile is substantially independent from the fluorescence of the bright microparticle, as well as from the type of buffer used and the exposure conditions.

In a further step, a chosen model is fitted to the relative fluorescence decay profile. More particularly, the sum of exponentials of relation (7) is chosen as the model, and in particular a sum of three exponentials. This model, while flexible, still provides an analytical expression between the relative crosstalk fluorescence and the distance from center of the bright microparticle. The profile of relative fluorescence decay has a complicated shape that may be hard to fit with a sum of three exponentials (plateau from 0 to ~50 pixels then sharp slope up to 85). Therefore, in order to increase the goodness of fit of the model, the data of the sharp slope are discarded. This is justified by the fact that distance corresponding to the sharp slope won't be filled with any other microparticles. For example, in the Evalution™ system, the radius of microparticle is approximatively of 56 pixels and therefore, the minimum distance between two microparticles is not expected to be smaller than 85 pixels. The model use to fit the data is thus in the Evalution™:

$$\alpha_{ij} = \sum_{n=1}^{3} \left(\theta_n \cdot e^{-k_n(d_{i,j}-85)}\right)$$

Figure 7:
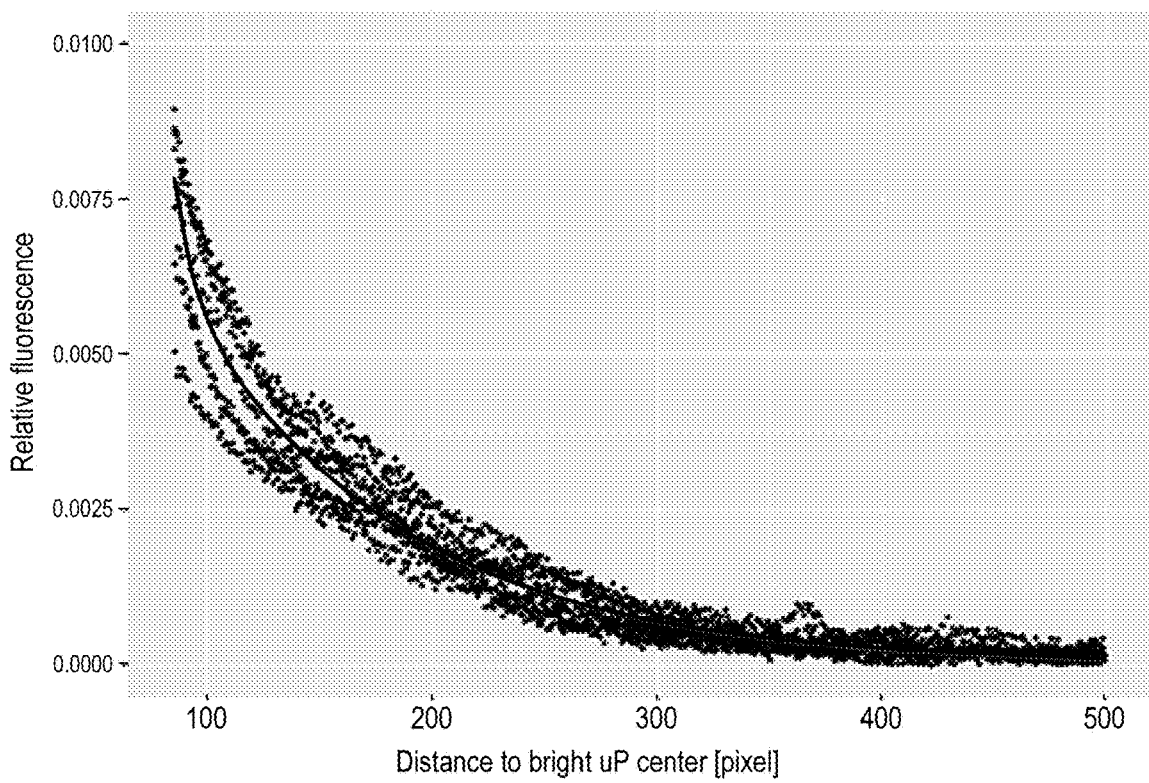
FIG. 7 illustrates a model fitted to the relative fluorescence decay profile.
Figure 8A:
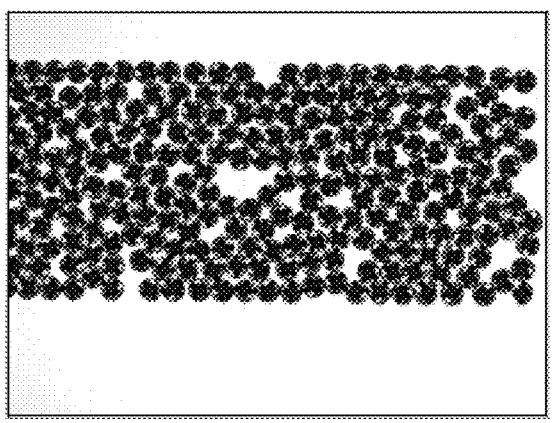
FIGS. 8A to 8D illustrate a bi-plex assay with bright and dark microparticles.
Figure 8B:
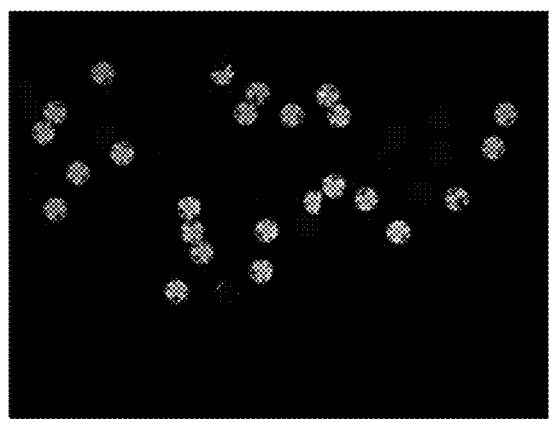
Figure 8C:
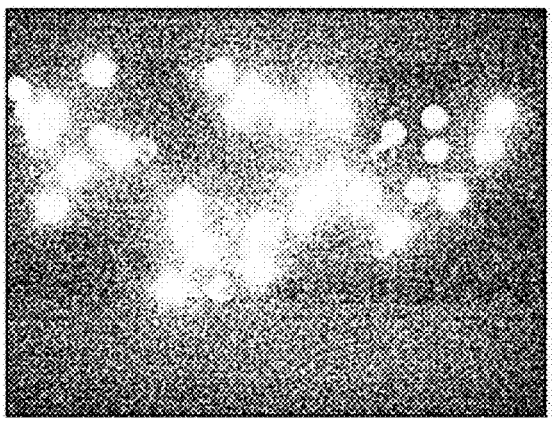
Figure 8D:
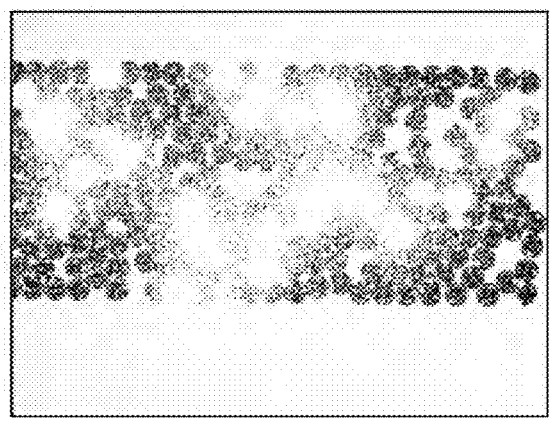

FIG. 7 shows a detail of the relative fluorescence decay of FIG. 6 with the red line corresponding to the fitted model. Obviously, any suitable model may be used.

Figure 9:
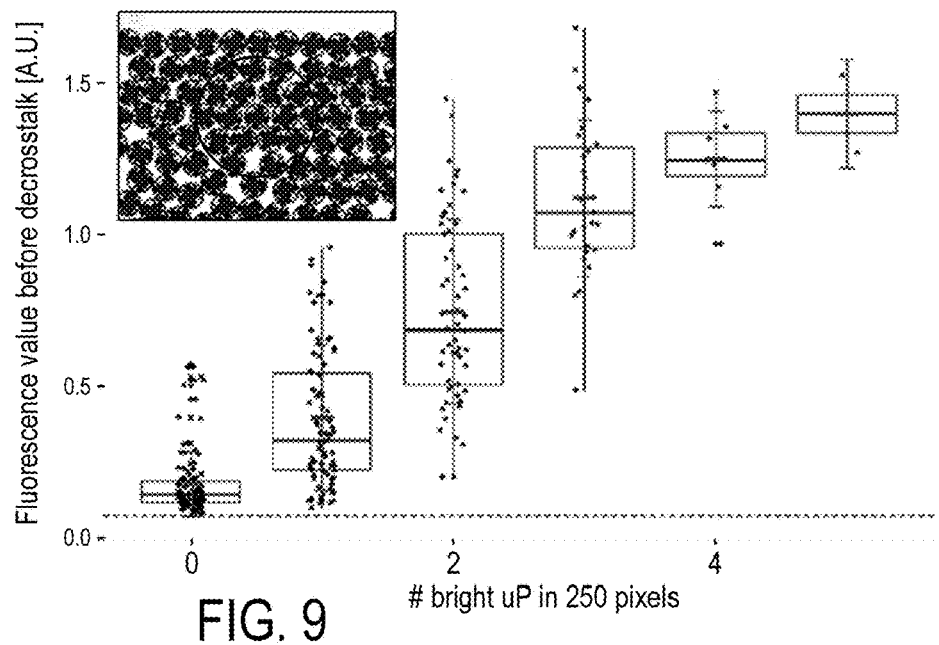
FIGS. 9 and 10 illustrate the effect in the measured bi-plex fluorescence of the cross-talk effect.

Example of the cross-talk effect correction is illustrated in relation with FIGS. 8 to 12. This example corresponds to a bi-plex assay, and thus two types of microparticles or populations, with a first population of microparticles (biotin-RPE microparticles) being very bright compared to a second population of microparticles (COOH microparticles). A bright field image of a channel receiving the two populations is illustrated in FIG. 8A. As it is illustrated in FIG. 8B, for standard image acquisition conditions (e.g. power of excitation=10 mW, exposure of the image acquisition=40 ms), the population fluorescence of the bright microparticles equals 112 A.U. ("Arbitrary Unit"). Having a close look to FIG. 8B, biotin-RPE microparticles are sharp, with no halo of light surrounding them, so that it is difficult to figure out cross-talk phenomenon takes place. However, by increasing the contrast of the fluorescence image 8B at its maximum (e.g. considering that image are coded on 8 bits, every pixels with original fluorescence greater or equal to is set value 255 and the pixels originally at 0 stay at 0), the crosstalk effect becomes apparent (FIG. 8C). Superimposing FIG. 8A and FIG. 8C (FIG. 4D), one notes the halos of the biotin-RPE microparticles overflow the COOH microparticles. FIG. 9 illustrates the aggregate fluorescence $\varphi_{COOH}^{pop}$ of the COOH population computed based on the measured fluorescences $\varphi_{COOH}^{meas}$ of COOH microparticles belonging to a circle of 250 pixel radius, as illustrated in the upper left part of FIG. 9. Aggregate fluorescence $\varphi_{COOH}^{pop}$ is here illustrated in function of the number of biotin-RPE microparticles in the circle. The fluorescence $\varphi_{COOH}^{pop}$ of the COOH population is positively correlated with the number of biotin-RPE microparticles, which illustrates the cross-talk phenomenon.

Figure 10:
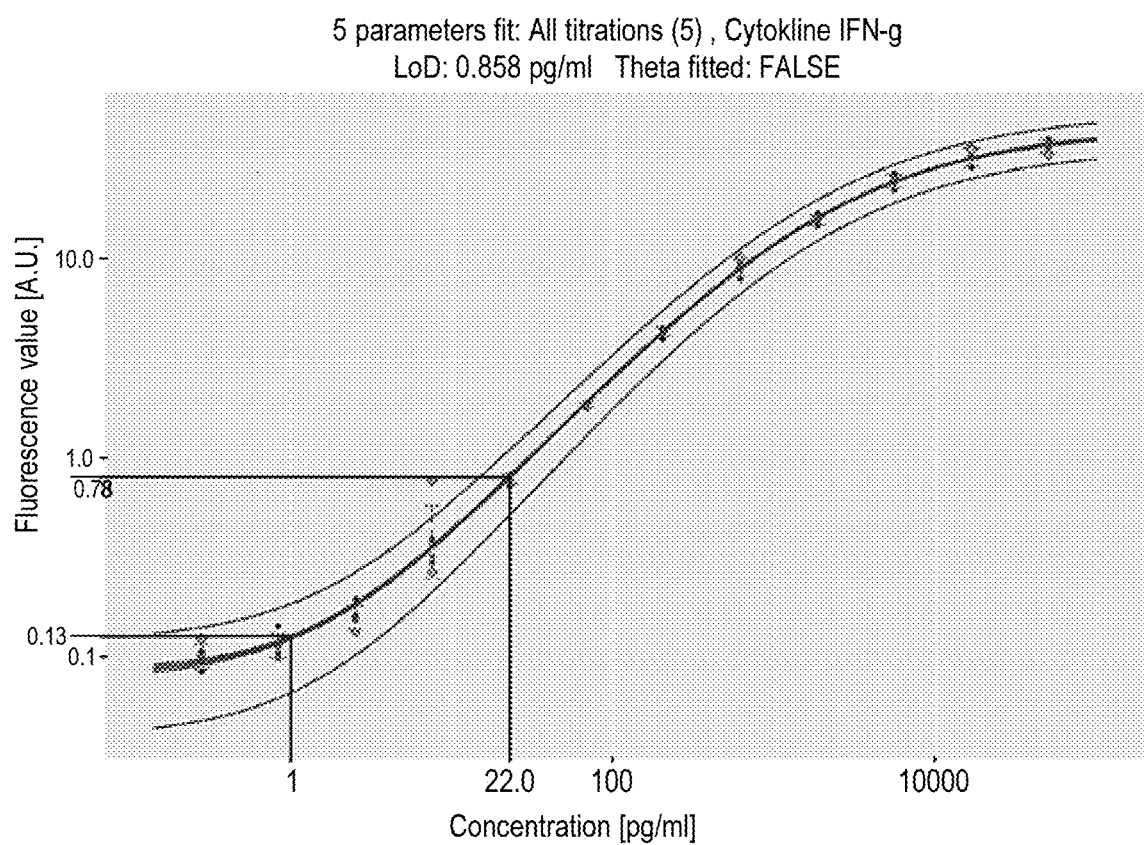

In particular, cross-talk effect results in an increasing of the $\varphi_{COOH}^{pop}$ value as it is illustrated by the horizontal dashed line which corresponds to the population fluorescence of COOH microparticles in a monoplex assay under the same acquisition conditions (0.07 A.U.). For example, with one biotin-RPE microparticle, the population fluorescence $\varphi_{COOH}^{pop}$ of COOH population equals 0.44 A.U. i.e. a six fold increase of the monoplex value. This dependence of population fluorescence to the fluorescence of the other populations in a multiplex is detrimental to the assay precision and might notably induce false positive results. For example, in a cytokine assay, a population fluorescence of 0.07 A.U. for INF-g is considered as not significantly above the blank fluorescence and therefore called negative. However a population fluorescence of 0.44 A.U. is well above the limit of detection and corresponds to an estimated concentration of 10.3 pg/ml. FIG. 10 illustrates the extrapolation of a six fold increase of fluorescence on a IFN-g experiment and its impact on the estimated concentration using the calibration curve used to transform population fluorescence $\varphi_{COOH}^{pop}$ into INF-g concentration.

After application of the cross-talk effect correction, the fluorescence measured on COOH microparticles should not be impacted by the fluorescence of bright microparticles present in the same field of view. In order to verify this independence, the population fluorescence of COOH microparticles in multiplex assays is compared to a reference value. The reference value is the corresponding population fluorescence of COOH measured in a monoplex assay under the same experimental condition.

The statistics used for the comparison between COOH in monoplex and multiplex assays is the ratio:

$$\rho = \frac{\varphi_m^{ag}(\text{multiplex})}{\varphi_m^{ag}(\text{simplex})}$$

If the signal intensity of COOH microparticles is not impacted by the presence of the bright microparticles, the ratio $\rho$ should be equal to one. In case of crosstalk between fluorescent and COOH microparticles, the ratio is expected to be greater than. Ratios $\rho$ have to be computed before and after decrosstalk in order assess the improvement of signal robustness to the plex level induced by the cross-talk effect correction.

Figure 11:
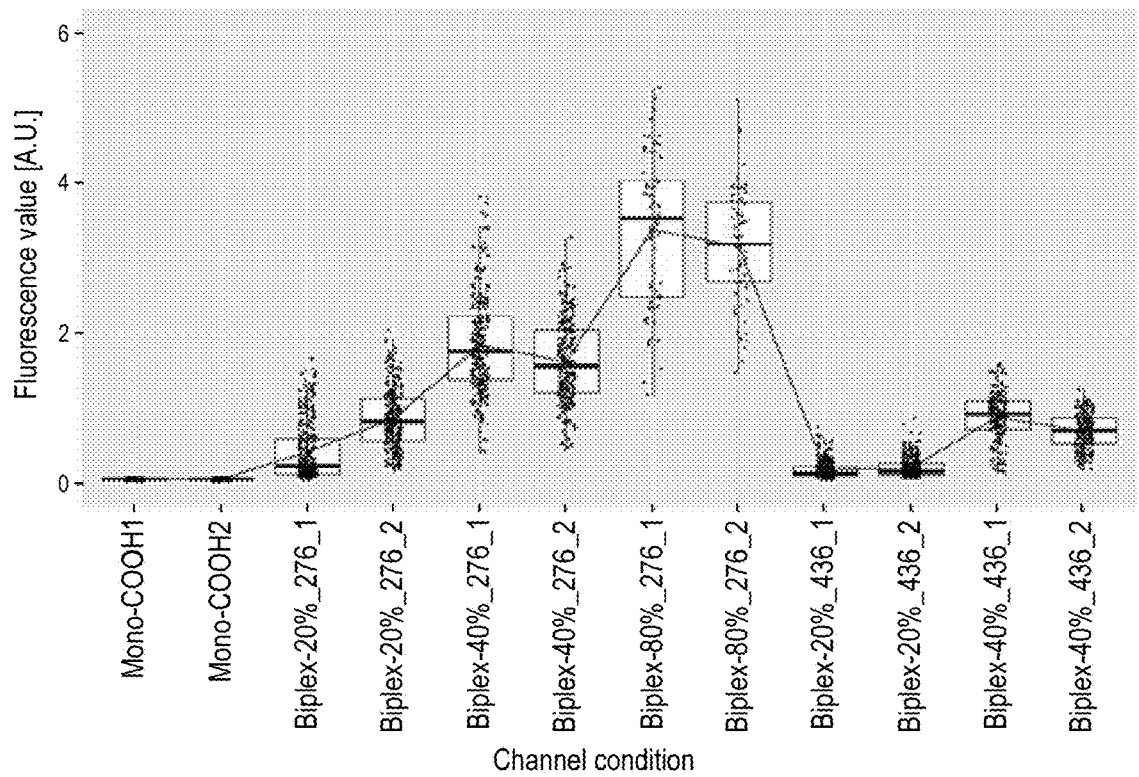
FIGS. 11 and 12 illustrate respectively the fluorescence of the dark microparticles before and after the cross-talk effect correction.
Figure 12:
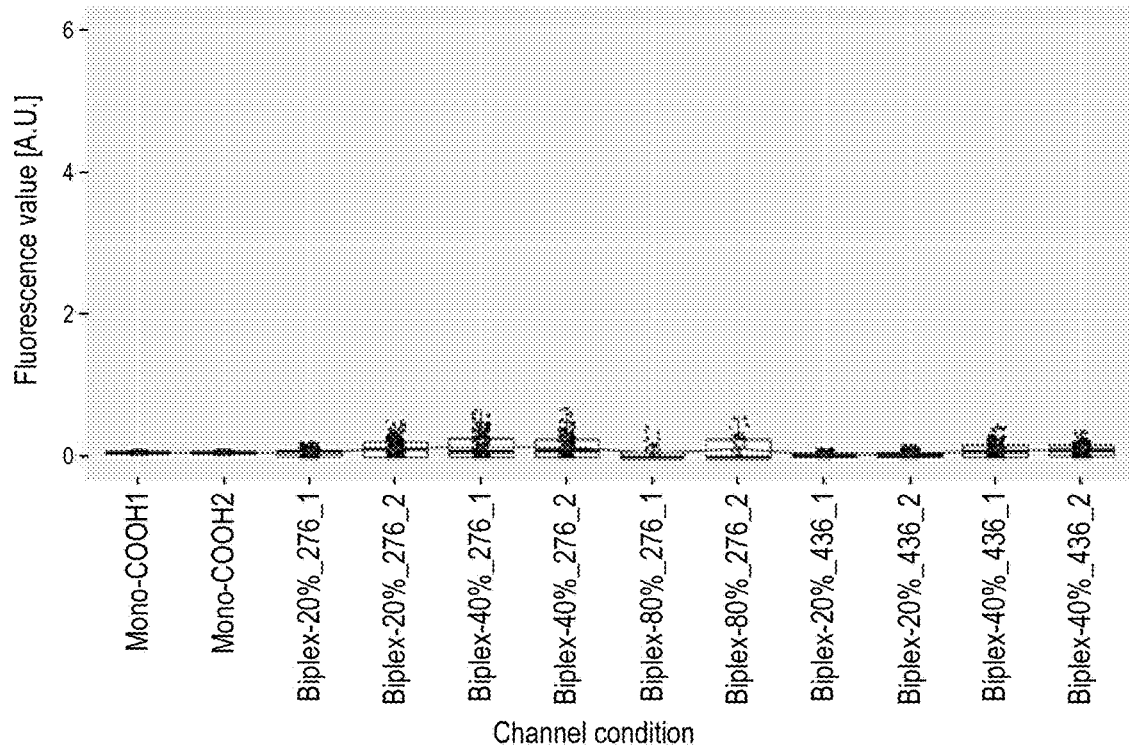

FIGS. 11 and 12 illustrate fluorescence measured on the COOH microparticles respectively before and after the cross-talk effect correction. The first two boxplots, on the left of the figures, present the fluorescence values in the monoplex assay. The following boxplots on the right present the COOH fluorescence values in the various biplex conditions (different ratios of bright/COOH microparticles). The labels on the x-axis contain the information of the approximate percentage of bright microparticle in the channel and the code type of bright microparticles present in the biplex (276 for 100% biotin-RPE coupled microparticles and 436 for 500% biotin-RPE coupled microparticles).

From FIG. 11, one observes that the uncorrected COOH fluorescence presents a strong correlation with the percentage of bright microparticle in the channel. The COOH population fluorescence in channels where 80% of the microparticles are 100%-biotin-RPE is more than 40 times higher than their population value in monoplex channels. As visible in FIG. 12, the correlation is significantly reduced after application of the decrosstalking algorithm. For example the ratios for the channels with 80% of bright microparticles are respectively reduced to 0.87 and 1.71. Qualitatively, the boxplots for the other experimental conditions (exposure time, type of buffer or out of focus configurations) present the same behavior.

The invention claimed is:

1. A method for determining fluorescence values $\{\varphi_i^{spe}\}_{i\in\{1, 2, \ldots, I\}}$ of a set of I fluorescent microparticles $\{\mu P_i\}_{i\in\{1, 2, \ldots, I\}}$ of a multiplexed analysis configured to detect multiple fluorescently labeled biomarkers, said microparticles being in a monolayer arrangement and encoded in silicon micro-disks carrying a binary code, the method comprising:

acquiring a digital fluorescence image of the set of fluorescent encoded microparticles $\{\mu P_i\}_{i\in\{1, 2, \ldots, I\}}$;

computing, for each fluorescent encoded microparticle $\mu P_i$ in the set of fluorescent encoded microparticles $\{\mu P_i\}_{i\in\{1, 2, \ldots, I\}}$, a fluorescence value $\varphi_i^{meas}$ based only on pixels of the acquired image corresponding to said fluorescent encoded microparticle $\mu P_i$, and obtaining the fluorescence value $\varphi_i^{spe}$ of said fluorescent encoded microparticle $\mu P_i$ using each fluorescence values $\varphi_i^{meas}$;

wherein the method comprises computing the fluorescence value $\varphi_i^{spe}$ of said fluorescent encoded microparticle $\mu P_i$ by correcting its first fluorescence $\varphi_i^{meas}$ by a cross-talk fluorescence contribution $\varphi_i^{cross}$, wherein the cross-talk fluorescence contribution $\varphi_i^{cross}$ is modeled as a sum of individual contributions, each having an isotropic decay profile:

$$\varphi_i^{cross} = \sum_{j\neq i}(\alpha_{i,j}\cdot\varphi_j^{spe})$$

wherein:
$\alpha_{i,j}$ is a unitary cross-talk fluorescence contribution in the first fluorescence $\varphi_i^{meas}$ of the $j^{th}$ fluorescent microparticle $\mu P_j$ depending only on the distance $d_{i,j}$ between microparticles $\mu P_i$ and $\mu P_j$ and predetermined parameters that are identical whatever the microparticles, the $j^{th}$ set of encoded microparticles is a subset created from the set of encoded microparticles $\{\mu P_i\}i\varepsilon\{1, 2, \ldots, I\}$ other than $\mu P_i$, and $\varphi_j^{spe}$ is the fluorescence of the $j^{th}$ fluorescent encoded microparticle $\mu P_j$.

2. A method as claimed in claim 1, wherein the computation of the fluorescence value $\varphi_i^{spe}$ comprises:

computing a position $X_i$ in the digital fluorescence image for each fluorescent encoded microparticle $\mu P_i$ in the set of fluorescent encoded microparticles $\{\mu P_i\}_{i\in\{1, 2, \ldots, I\}}$;

modelling the first fluorescence value $\varphi_i^{meas}$ as a function of the positions $\{X_i\}_{i\in\{1, \ldots, I\}}$ and fluorescence values $\{\varphi_i^{spe}\}_{i\in\{1, \ldots, I\}}$ of all fluorescent encoded microparticles $\{\mu P_i\}_{i\in\{1, 2, \ldots, I\}}$; and computing the inverse of said function to obtain the fluorescence value $\varphi_i^{spe}$.

3. A method as claimed in claim 1, wherein the method comprises:

computing the distance $d_{i,j}$ between the $i^{th}$ and the $j^{th}$ fluorescent encoded microparticles in the digital fluorescence image;

for each couple of encoded microparticles $(\mu P_i, \mu P_j)$ in the set of I fluorescent encoded microparticles, computing the unitary cross-talk fluorescence contribution $\alpha_{i,j}$ of said couple $(\mu P_i, \mu P_j)$ based on the distance $d_{i,j}$;

computing the fluorescences $\{\varphi_i^{spe}\}_{i\in\{1, 2, \ldots, I\}}$ of the set of fluorescent encoded microparticles $\{\mu P_i\}_{i\in\{1, 2, \ldots, I\}}$ based on the following relationship:

$$\begin{pmatrix} \varphi_1^{spe} \\ \varphi_2^{spe} \\ \vdots \\ \varphi_{I-1}^{spe} \\ \varphi_I^{spe} \end{pmatrix} = \begin{pmatrix} 1 & \alpha_{12} & \cdots & \alpha_{1(I-1)} & \alpha_{1I} \\ \alpha_{21} & 1 & \cdots & \alpha_{2(I-1)} & \alpha_{2I} \\ \vdots & & \ddots & & \vdots \\ \alpha_{(I-1)1} & \alpha_{(I-1)2} & \cdots & 1 & \alpha_{(I-1)I} \\ \alpha_{I1} & \alpha_{I2} & \cdots & \alpha_{I(I-1)} & 1 \end{pmatrix}^{-1} \begin{pmatrix} \varphi_1^{meas} \\ \varphi_2^{meas} \\ \vdots \\ \varphi_{I-1}^{meas} \\ \varphi_I^{meas} \end{pmatrix}.$$

4. A method as claimed in claim 1, wherein each fluorescent encoded microparticle $\mu P_i$ of the set of fluorescent encoded microparticles $\{\mu P_i\}_{i \in \{1, 2, \ldots, I\}}$ comprises an identifier $Id_m(i)$ of a set of M different unique identifiers $\{id_m\}_{m \in \{1, 2, \ldots, M\}}$, said identifiant $Id_M(i)$ being readable through processing of a digital image of said fluorescent encoded microparticle $\mu P_i$, and in that the method further comprises:

- acquiring a digital image of the set of fluorescent encoded microparticles $\{\mu P_i\}_{i \in \{1, 2, \ldots, I\}}$;
- reading the identifier $Id_m(i)$ of each encoded microparticle $\mu P_i$ in the digital image; and
- for each identifier $Id_m$ of the set of M different unique identifiers $\{id_m\}_{m \in \{1, 2, \ldots, M\}}$, computing an aggregate fluorescence $\varphi_m^{ag}$ based on the fluorescences $\varphi_i^{spe}$ of the fluorescent encoded microparticles comprising said identifiant.

5. A method as claimed in claim 4, wherein each fluorescent encoded microparticle $\mu P_i$ of the set of fluorescent encoded microparticles $\{\mu P_i\}_{i \in \{1, 2, \ldots, I\}}$ comprises a surface coated with fluorescent complexes uniquely associated to the identifier $Id_m(i)$ of said fluorescent encoded microparticle $\mu P_i$, said complexes comprising first non-fluorescent molecules fixed to the encoded microparticles and second fluorescent molecules bound to the first non-fluorescent molecules.

6. A method as claimed in claim 5, wherein the encoded microparticles have equal dimension.

7. A method as claimed in claim 5, wherein the method comprises:

- prior to acquiring the digital fluorescence image of the set of fluorescent encoded microparticles $\{\mu P_i\}_{i \in \{1, 2, \ldots, I\}}$;
  - disposing in a channel the microparticles without any second fluorescent molecules bound to the first non-fluorescent molecules, so as to arrange the microparticles in a monolayer; and
  - filling the channel with a liquid sample,
- computing concentration of second fluorescent molecules in the sample based on the aggregate fluorescences $\varphi_m^{ag}$.

8. A system for determining fluorescences $\{\varphi_i^{spe}\}_{i \in \{1, 2, \ldots, I\}}$ of a set of I fluorescent encoded microparticles $\{\mu P_i\}_{i \in \{1, 2, \ldots, I\}}$ being encoded in silicon micro-disks carrying a binary code comprising:

- at least one channel for receiving the set of I encoded microparticles $\{\mu P_i\}_{i \in \{1, 2, \ldots, I\}}$ in a monolayer arrangement;
- an acquisition unit for acquiring a digital fluorescent image of the monolayer arrangement of the set fluorescent encoded microparticles $\{\mu P_i\}_{i \in \{1, 2, \ldots, I\}}$ in the channel;
- a computing unit for computing the fluorescences $\{\varphi_i^{spe}\}_{i \in \{1, 2, \ldots, I\}}$ based on the acquired digital fluorescent image, the computing unit computing a first fluorescence $\varphi_i^{meas}$ based only on pixels of the acquired digital fluorescent image corresponding to said fluorescent encoded microparticle $\mu P_i$, said computing unit being configured to obtain the fluorescence value $\varphi_i^{spe}$ of a fluorescent encoded microparticle $\mu P_i$ using each fluorescence values $\varphi_i^{meas}$;

wherein the computing unit computes, for each fluorescent encoded microparticle $\mu P_i$ in the set of fluorescent encoded microparticles $\{\mu P_i\}_{i \in \{1, 2, \ldots, I\}}$:

- a cross-talk fluorescence contribution $\varphi_i^{cross}$, wherein the cross-talk fluorescence contribution $\varphi_i^{cross}$ is modeled as a sum of individual contributions, each having an isotrpic decay profile, based on the following relationship:

$$\varphi_i^{cross} = \sum_{j \neq i} (\alpha_{ij} \cdot \varphi_j^{spe})$$

wherein:

- $\alpha_{ij}$ is a unitary cross-talk fluorescence contribution in the first fluorescence $\varphi_i^{meas}$ of the $j^{th}$ fluorescent microparticle $\mu P_j$ depending only on the distance $d_{i,j}$ between microparticles $\mu P_i$ and $\mu P_j$ and predetermined parameters that are identical whatever the microparticles,
- the $j^{th}$ set of encoded microparticles is a subset created from the set of encoded microparticles $\{\mu P_i\}_{i \in \{1, 2, \ldots, I\}}$ other than $\mu P_i$, and $\varphi_j^{spe}$ is the fluorescence of the $j^{th}$ fluorescent encoded microparticle $\mu P_j$; and
- the fluorescence $\varphi_i^{spe}$ of said fluorescent encoded microparticle $\mu P_i$ by correcting its first fluorescence $\varphi_i^{meas}$ by the cross-talk fluorescence contribution $\varphi_i^{cross}$.

9. A system as claimed in claim 8, wherein the computing unit computes the fluorescence value $\varphi_i^{spe}$ by:

- computing a position $X_i$ in the digital fluorescence image for each fluorescent encoded microparticle $\mu P_i$ in the set of fluorescent encoded microparticles $\{\mu P_i\}_{i \in \{1, 2, \ldots, I\}}$;
- modelling the first fluorescence value $\varphi_i^{meas}$ as a function of the positions $\{X_i\}_{i \in \{1, \ldots, I\}}$ and fluorescence values $\{\varphi_i^{spe}\}_{i \in \{1, \ldots, I\}}$ of all fluorescent encoded microparticles $\{\mu P_i\}_{i \in \{1, 2, \ldots, I\}}$; and
- computing the inverse of said function to obtain the fluorescence value $\varphi_i^{spe}$.

10. A system as claimed in claim 8, wherein the computing unit:

- computes the distance $d_{i,j}$ between the $i^{th}$ and the $j^{th}$ fluorescent encoded microparticles in the digital fluorescence image;
- for each couple of encoded microparticles $(\mu P_i, \mu P_j)$ in the set of I fluorescent encoded microparticles, computes the unitary cross-talk fluorescence contribution $\alpha_{ij}$ of said couple $(\mu P_i, \mu P_j)$ based on the distance $d_{i,j}$;
- computes the fluorescences $\{\varphi_i^{spe}\}_{i \in \{1, 2, \ldots, I\}}$ of the set of fluorescent encoded microparticles $\{\mu P_i\}_{i \in \{1, 2, \ldots, I\}}$ based on the following relationship:

$$\begin{pmatrix} \varphi_1^{spe} \\ \varphi_2^{spe} \\ \vdots \\ \varphi_{I-1}^{spe} \\ \varphi_I^{spe} \end{pmatrix} = \begin{pmatrix} 1 & \alpha_{12} & \cdots & \alpha_{1(I-1)} & \alpha_{1I} \\ \alpha_{21} & 1 & \cdots & \alpha_{2(I-1)} & \alpha_{2I} \\ \vdots & \vdots & \ddots & \cdots & \vdots \\ \alpha_{(I-1)1} & \alpha_{(I-1)2} & \cdots & 1 & \alpha_{(I-1)I} \\ \alpha_{I1} & \alpha_{I2} & \cdots & \alpha_{I(I-1)} & 1 \end{pmatrix}^{-1} \begin{pmatrix} \varphi_1^{meas} \\ \varphi_2^{meas} \\ \vdots \\ \varphi_{I-1}^{meas} \\ \varphi_I^{meas} \end{pmatrix}.$$

11. A system as claimed in claim 8, wherein each fluorescent encoded microparticle $\mu P_i$ of the set of fluorescent encoded microparticles $\{\mu P_i\}_{i \in \{1, 2, \ldots, I\}}$ comprises an identifier $Id_m(i)$ of a set of M different unique identifiers $\{id_m\}_{m \in \{1, 2, \ldots, M\}}$ said identifiant $Id_M(i)$ being readable through processing of a digital image of said fluorescent encoded microparticle $\mu P_i$, and in that the computing unit:

- acquires a digital image of the set of fluorescent encoded microparticles $\{\mu P_i\}_{i \in \{1, 2, \ldots, I\}}$;

reads the identifier $Id_m(i)$ of each encoded microparticle $\mu P_i$ in the digital image; and for each identifier $Id_m$ of the set of M different unique identifiers $\{id_m\}_{m \in \{1, 2, \ldots, M\}}$ computes an aggregate fluorescence $\varphi_m^{ag}$ based on the fluorescences $\varphi_i^{spe}$ of the fluorescent encoded microparticles comprising said identifiant.

12. A system as claimed in claim 11, wherein each fluorescent encoded microparticle of the set of fluorescent encoded microparticles $\{\mu P_i\}_{i \in \{1, 2, \ldots, I\}}$ comprises a surface coated with fluorescent complexes uniquely associated to the identifier $Id_m(i)$ of said fluorescent encoded microparticle said complexes comprising first non-fluorescent molecules fixed to the encoded microparticles and second fluorescent molecules bound to the first non-fluorescent molecules.

13. A system as claimed in claim 12, wherein the encoded microparticles have equal dimension.

* * * * *